United States Patent [19]
Glaug et al.

[11] Patent Number: 5,217,448
[45] Date of Patent: Jun. 8, 1993

[54] ABSORBENT PRODUCTS HAVING OPTIONAL SIDE PANEL USAGE

[75] Inventors: Frank S. Glaug, Spotswood; Thomas Luceri, Nashanic Station, both of N.J.

[73] Assignee: McNeill-PPC, Inc., Milltown, N.J.

[21] Appl. No.: 568,937

[22] Filed: Aug. 17, 1990

[51] Int. Cl.⁵ .............................................. A61F 13/15
[52] U.S. Cl. .............................. 604/397; 604/385.1
[58] Field of Search ............................ 604/391–398, 604/385.1, 389

[56] References Cited

U.S. PATENT DOCUMENTS

| | | | |
|---|---|---|---|
| 4,589,876 | 5/1986 | Van Tilburg | 604/393 |
| 4,701,178 | 10/1987 | Glaug et al. | 604/387 |
| 4,862,574 | 9/1989 | Seidy | 604/398 |

FOREIGN PATENT DOCUMENTS

WO89/02729  4/1989  France.

OTHER PUBLICATIONS

EPO Search Report for European Application EP 91 30 7580, Nov. 11, 1991.

Primary Examiner—Randy C. Shay
Assistant Examiner—G. Gualtieri

[57] ABSTRACT

Sanitary napkins are provided which include release surfaces disposed on their undergarment-facing side so that adhesive elements on one or more flaps can be secured. This feature provides users of the sanitary napkin product with the choice of employing side-protecting flaps upon demand or leaving them in place. The napkins also incorporate preferred adhesive element systems which can be disposed to contact silicone treated films or other release areas on their undergarment-facing sides. Additional embodiments of this invention provide for extending the release surface to enable tri-folding of the napkin and a partial or total elimination of traditionally required release paper strips.

17 Claims, 2 Drawing Sheets

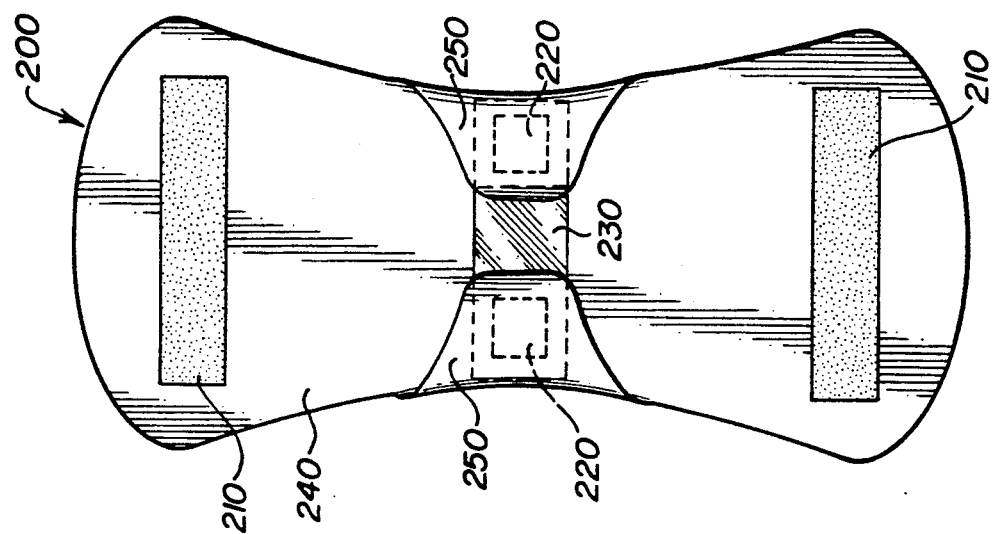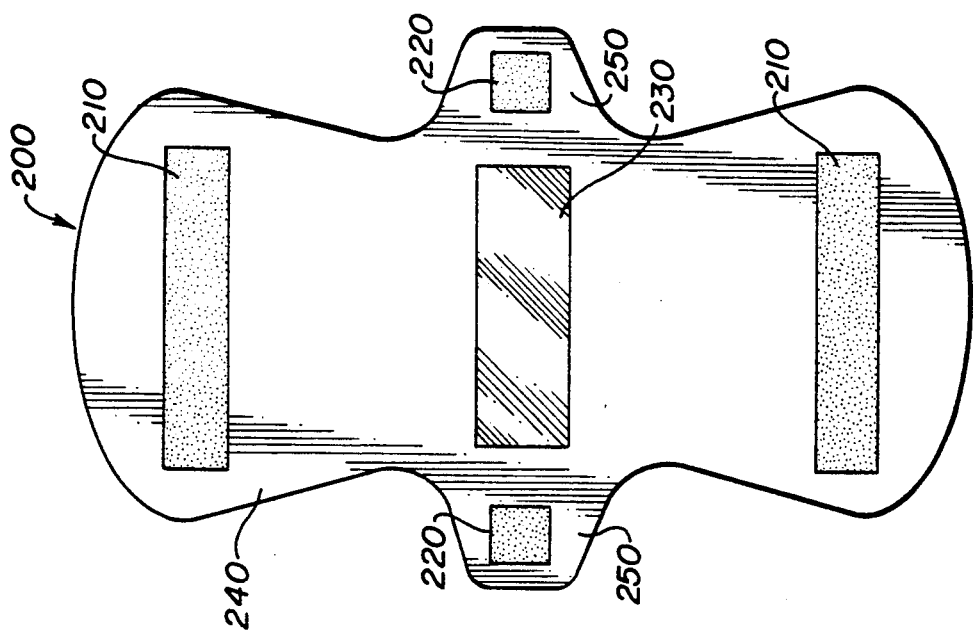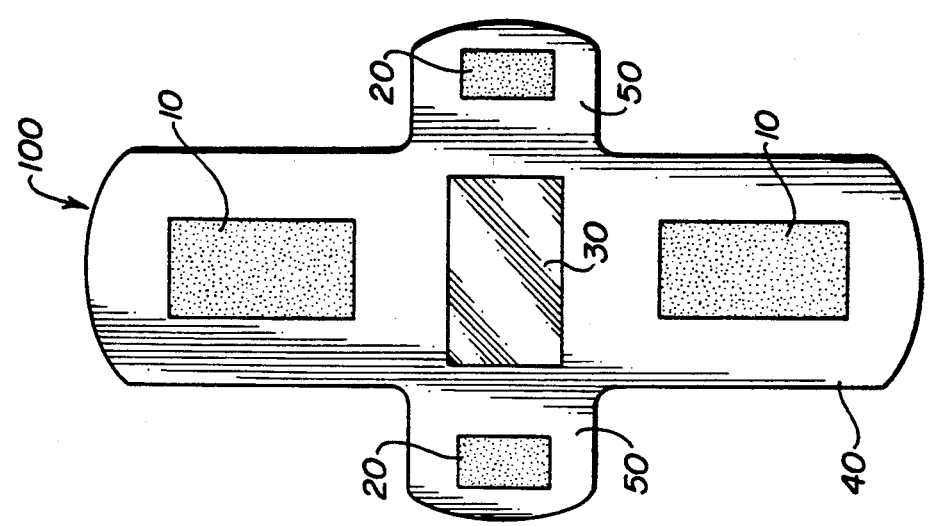

ABSORBENT PRODUCTS HAVING OPTIONAL SIDE PANEL USAGE

FIELD OF THE INVENTION

This invention relates to absorbent products for absorbing body fluids, and in particular, to products intended to be worn against the perineal portion of the body and held in place by attachment to the crotch portion of an undergarment worn by a user. Such products find wide application as sanitary napkins, panty shields, panty liners and adult incontinence pads.

BACKGROUND OF THE INVENTION

Sanitary napkins traditionally have incorporated a central and absorbent having a permeable body-facing side and a liquid resistant, undergarment-facing side. Such napkins are typically applied to the inside crotch area of an undergarment with one or more pressure-sensitive adhesive strips.

More recently, sanitary napkins having side panels or flaps which laterally extend a short distance from the central absorbent and are intended to be folded about the outer crotch portion of the undergarment. See Mattingly, U.S. Pat. No. 4,608,047, issued Aug. 26, 1986, and Glaug, et al., U.S. Pat. No. 4,701,178, issued Oct. 20, 1987, both of which are hereby incorporated by reference.

The side-protecting flaps of Glaug are adhered to a release strip during packaging. Such release strips, however, present a significant waste disposable problem as well as contribute to a more expensive sanitary napkin.

Mattingly does not employ a release strip, but rather, adheres the flaps together using the pressure-sensitive adhesive element designed for permitting the flaps to be attached to one another once they have wrapped around the crotch of an undergarment. Adhering flaps to one another for "packaging" purposes, however, without appropriate safeguards, can present a risk of damaging the impervious backing materials of the flaps when a user attempts to disengage them prior to use.

Accordingly, a need exists for absorbent products that contain side panels or side-protecting flaps which can be secured to the product for selective use and convenient packaging. There is also a need for minimizing disposal problems associated with release paper which normally covers flap adhesive elements.

SUMMARY OF THE INVENTION

In accordance with the teachings of this invention, improved sanitary napkins are provided having a central absorbent element which includes a fluid permeable, body-facing side and a fluid resistant, undergarment-facing side. The napkins further include at least one flap extending laterally from the sides of the central absorbent element. This flap has adhesive means disposed for securing the sanitary napkin to the outer crotch area of an undergarment. The undergarment-facing side of the napkins of this invention includes a release surface means for securing at least a portion of the flap adhesive means during packaging.

Accordingly, the napkins of this invention permit the side flaps to remain adhered to the release surface for consumers who do not prefer side panel protection. Alternatively, for those individuals who choose the added protection of flaps, the side flap or flaps can be detached from the release surface on the undergarment-facing side of the central absorbent and wrapped around and secured to an undergarment. Such a single product would therefore appeal to both types of sanitary napkin users.

The integral release surface means described herein provides an effective and efficient means for adhering one or more flaps to the undergarment-facing side of the absorbent element during packaging. Additionally, because a separate release paper strip for protecting the flap adhesive means is not necessary, the product can present a cost savings for the manufacturer.

BRIEF DESCRIPTION OF THE DRAWINGS

The accompanying drawings illustrate preferred embodiments of the invention for the practical application of the principles thereof, and in which;

FIG. 1: is a planar view of the undergarment-facing side of a sanitary napkin embodiment of this invention having traditional styling, but illustrating a preferred adhesive system and a release surface area;

FIG. 2: is a planar view of an undergarment-facing side of another sanitary napkin embodiment of this invention having an hourglass design and light weight construction, and further illustrating an adhesive system and release surface area;

FIG. 3: is a planar view of the undergarment-facing side of the sanitary napkin embodiment of FIG. 2 illustrating how the flap adhesive elements can be secured to the release surface area.

DETAILED DESCRIPTION OF THE INVENTION

Figure 4:
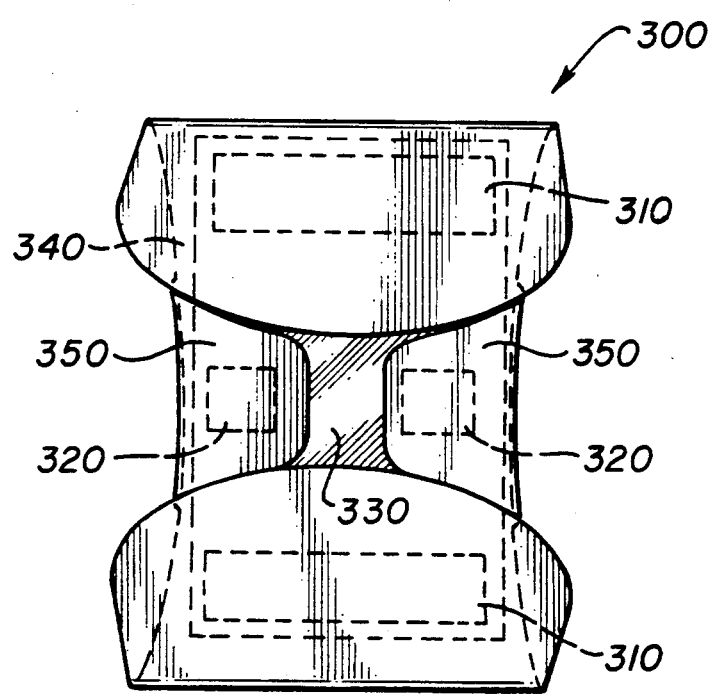
FIG. 4: is a planar view of the undergarment-facing side of an hourglass napkin embodiment illustrating a larger release surface area for attachment of the adhesive elements of the flaps and the transverse ends of the napkin for packaging or disposal.

This invention provides absorbent products, such as sanitary napkins which include an central absorbent element having longitudinally extending sides, transverse ends, a body-facing side and an undergarment-facing side. The undergarment-facing side of the central absorbent element includes a release surface means. Extending laterally from one or more longitudinal sides of the central absorbent elements of this invention are one or more flaps. At least one of these flaps includes adhesive means disposed to contact the release surface means as the flap folded onto the undergarment-facing side of the central absorbent element, for example, during packaging.

In a more detailed embodiment of this invention, a sanitary napkin is provided having an central absorbent element having a body-facing side and an undergarment-facing side. Onto the undergarment-facing side of this embodiment are disposed a pair of adhesive elements and a release surface disposed between the adhesive elements such that when the transverse ends of the napkin are folded onto the undergarment-facing side of the central absorbent element, the adhesive elements are disposed to contact the release surface. This napkin embodiment further includes flaps extending laterally from each of the longitudinal sides the central absorbent element. Each of these flaps includes individual adhesive elements disposed to contact a release surface when the flaps are folded onto the undergarment facing side of the absorbent element. This particular sanitary napkin can be conveniently tri-folded for convenient and compact packaging.

This invention also provides a method for applying a sanitary napkin to an undergarment which includes the step of providing a sanitary napkin having an undergarment-facing side which includes adhesive means and a release surface disposed approximately midway between the transverse ends of the napkin. The release surface means can be a silicone composition which is coated onto the barrier means and cured. The silicone composition may be cured by electron-beam radiant energy, ultraviolet energy or heat. Flaps are provided on the napkin which extend laterally from each of the longitudinal sides of the central absorbent element and further include individual adhesive means. The flaps are folded onto the undergarment facing side of the central absorbent element so as to releasably attach the individual adhesive means of each of the flaps to the release surface of the central absorbent element. Pursuant to this method, the adhesive means of the absorbent element can be attached to the undergarment, with or without adhering the individual adhesive means of the flaps to the outside portion of the undergarment or, in the case where the flaps have sufficient lateral length to each other.

With reference to the drawings, and particularly to FIGS. 1 and 2 thereof, there is shown preferred sanitary napkins 100 and 200 having central absorbent elements and flaps 50 and 250. Disposed proximate to the transverse end of these napkins are adhesive elements 10 and 210 for securing the napkins 100 and 200 to the inner crotch portion of an undergarment. These embodiments also include individual adhesive elements 20 and 220 for adhering the flaps to an outer portion of an undergarment. The napkin embodiments 100 and 200 further include a release surface 30 and 230 for adhering to adhesive elements 20 and 220 during packaging or when side-protecting flaps are not desired, such as described in FIG. 3.

Referring now to FIG. 4, a tri-folding technique will now be described. This particular embodiment employs a release surface element 230 which is substantially larger than those previously described. Thus, the transverse ends of the napkin 300 can be folded onto the undergarment-facing side 340 such that the attachment adhesive elements 310 are joined to release surface element 330. As illustrated, the flaps 350 can also be disposed onto the release surface element 330 substantially as described. Thus, the entire napkin 300 can be conveniently packaged without any release paper at all. This tri-folding capability also enables a user to conveniently fold a soiled napkin for disposal.

The release surface elements of this invention, such as preferred elements 30, 230 and 330 are preferably located approximately midway between the transverse ends of the napkins. These elements can comprise treated portions of the undergarment-facing side 40, 240 and 340 of the central absorbent elements, or a separate sheet, such as a thermoplastic polyethylene web, affixed to the undergarment-facing side of the napkin, i.e., via adhesive, ultrasonic or thermal bonding. The release surface is preferably fabricated with a silicone treatment, although other chemical or mechanical treatments known to those of ordinary skill are within the scope of this concept. In the preferred embodiments, the release surface elements 30, 230 and 330 include a polyethylene web coated with silicone and having a thickness of about 0.01 to about 0.125 inches (0.025–3.11 mm).

The central absorbent elements of this invention may be constructed with any of the well known absorbent materials used in products for absorbing body fluids such as, for example, loosely associated absorbent hydrophilic material such as cellulose fibers, e.g., wood pump, regenerated cellulose or cotton fibers. Such fibers may be chemically or physically modified and the absorbent element may include such fibers in combination with other materials, both natural, such as sphagnum moss, and synthetic, such as hydrophilic foams, hydrophilic polymers or the like. Wood pulp is frequently the material of choice primarily because it is inexpensive and readily available.

The central absorbent element may also comprise layers of materials which in the aggregate are body fluid absorbent. For example, the outermost layer (closest to the body) may be a resilient, relatively non-absorbing, fluid previous material. Such a material is provided for comfort and conformability and directs fluid to an underlying layer, e.g. wood pulp, which retains such fluid. A useful material for this outer layer is hollow polyester fibers having a denier of about 8.5 and a length of about 1.5 inches.

Overlying the body-facing side of the central absorbent elements of this invention preferably is a fluid permeable cover material. This cover material may comprise any of the well known liquid pervious materials used in sanitary napkins including, for example, non-woven fabrics of cellulose, regenerated cellulose, polyester, polyethylene, or other synthetic polymers. Additionally, polymeric fibers or films having apertures therethrough to render the materials previous to fluids may also be employed. A cover material of choice is a fabric comprising heat bondable polyester/-polyethylene conjugate fibers.

The central absorbent element, in accordance with the more traditional design of FIG. 1, is preferably wrapped in and adhered to an elongated C-shaped wrap or cover of fluid impervious material. See U.S. Pat. No. 4,701,178. The fluid impervious material preferably comprises a polyethylene "boat" which is adhered to the central absorbent element by an emulsion adhesive. The purpose of the polyethylene boat is fluid containment, whereby fluid will not be transferred from the undergarment-facing side and edges of the central absorbent element to an outer location where it could stain the undergarments of the user. The preferred polyethylene boat extends beyond the longitudinal ends of the central absorbent element. The boat is preferably sealed at the ends and adhered to a body fluid impervious barrier which constitutes the undergarment-facing side of the napkins. The barrier is provided to preclude body fluid from passing onto the undergarment of the wearer. The barrier, like the boat, may be any polymeric film such as a polyethylene, polypropylene, or cellophane or may be a normally fluid-pervious material that has been treated to be impervious such as a fluid repellent paper. When the boat and the barrier are made of heat bondable materials the boat may be advantageously thermally or ultrasonically sealed at its ends and to the barrier.

The preferred flaps of this invention 50, 250 and 350 preferably extend out from the longitudinal edges of the barrier. As will become apparent from the further description, the flaps extend a sufficient degree to enable them to overlie the outer crotch portion of the wearer's undergarment. The flaps may be constructed of a sufficient lateral length so that they overlap each other after they are wrapped around the crotch area of the undergarment. With flaps extended in this fashion, adhesive elements attached to the flap or flaps can be used to attach the flaps to one another. See U.S. Pat. No. 4,608,047. The preferred flaps are provided for two primary purposes, namely to more fully protect the user's undergarment from liquid escaping from the central absorbent element along its longitudinal edges and to act as an attachment system to hold the central absorbent element firmly in place as it moves together with the crotch of the undergarment during the wearer's movements.

Absorbent material may be included within the flaps 50, 250 and 350 and may comprise a thin, absorbent layer of material such as tissue, fabric, or the like, made of cellulosic fibers. This material is provided so that any escaped fluid from the central absorbent element may be absorbed and prevented from flowing across the flaps and onto the body or garment of the wearer. Since the absorbent material layer preferably covers the body-facing side of the flaps, it also provides a degree of comfort in the crotch area. Because such material is provided as a safety measure and is only required to retain escaped fluid, it need not be very absorbent at all and, in fact, may be comprised of any capillary or cellular system including hydrophobic material. Thus, a useful material may be a 0.5 oz./yd.$^2$ fabric comprised of hollow polyester fibers and heat bondable polyester/polyethylene conjugate fibers. Such conjugate fibers are fibers which comprise a polyester core surrounded by a sheath of Polyethylene. Although it is not composed of hydrophilic fibers, such a material may be formed of a sufficiently fine capillary structure so as to retain small quantities of escaped liquid and hence be sufficiently "absorbent" for its intended purpose as a safety measure.

When the absorbent layer and the barrier material of the central absorbent element are both formed of thermoplastic material as described above, the napkin may be advantageously assembled by heat sealing or ultrasonic sealing. The absorbent layer surface of the flaps preferably is thermally sealed to the opposing longitudinal edges of the cover, and the barrier material of the flaps is preferably thermally sealed to the opposing edges of the barrier of the central absorbent element. In a preferred embodiment, the barrier and the barrier material comprise sheets of 1.5 mil embossed polyethylene. However, the thickness may be greater so long as the barrier material is flexible and comfortable in use.

The preferred adhesive elements of this invention 10, 210, 310, 20, 220, and 320 preferably include pressure-sensitive adhesive. While such adhesive means are illustrated in the form of longitudinally extending lines, it will be understood that various patterns such as spots, squares, or transverse lines are suitable. The adhesive employed may be any of the large number of pressure-sensitive adhesives that are commercially available, including water-based adhesives such as acrylate adhesives, e.g., vinyl acetate/2-ethylhexyl acrylate copolymer which may be combined with tackifiers. Alternatively, the adhesive may also comprise a pressure-sensitive rapid-setting hot melt adhesive such as Fuller 6680 produced by the H.B. Fuller Co. The adhesive means may also comprise a double faced tape.

In a more preferred embodiment of this invention, an hourglass shaped sanitary napkin is provided having a light-weight construction, such as that described FIGS. 2 and 3. In this embodiment, the C-shaped boat is eliminated and a longitudinally-cut, sphagnum moss, absorbent element is employed. The sphagnum moss absorbent element is preferably sandwiched between an embossed fluid permeable cover, such as non-woven layer of cellulose or polyester-polyethylene congregate fibers, and a polyethylene, fluid impervious barrier. The cover and barrier are then heat or ultrasonically sealed about the periphery of the hourglass shape to seal in the sphagnum moss absorbent element. Flaps are provided in this light construction by extending the barrier and cover laterally from the central absorbent and then heat sealing and cutting these joined members into a flap shape. This construction is substantially thinner than the conventional sanitary napkin earlier described, and can be an attractive alternative product.

The foregoing demonstrates that the sanitary napkins of this invention provide optional side panel usage, while simultaneously minimizing the cost of manufacturing these products by eliminating typically employed release paper. The overall napkin is more compact and suitable for tri-folding during packaging and disposal. Although various embodiments have been illustrated, this was for the purpose of describing, but not limiting the invention. Various modifications, which will become apparent to one skilled in the art, are within the scope of this invention described in the attached claims.

What is claimed is:

1. A sanitary napkin comprising:
   (a) a central absorbent element having longitudinally extending sides, transverse ends, a body-facing side and an undergarment-facing surface, said undergarment-facing surface including release surface means, said release surface means being permanently attached to said undergarment-facing surface; and
   (b) a flap extending laterally from one of said longitudinal sides of said central absorbent element, said flap comprising adhesive means disposed to contact said release surface means when said flap is folded onto said undergarment-facing surface of said central absorbent element.

2. The sanitary napkin of claim 1 further comprising a second flap extending laterally from another one of said longitudinal sides of said central absorbent element, said second flap comprising a second adhesive means disposed to contact said release surface means when said second flap is folded onto said undergarment-facing surface of said central absorbent element.

3. The sanitary napkin of claim 2 wherein said release surface means comprises a silicone treated portion of said undergarment-facing surface central absorbent element.

4. The sanitary napkin of claim 2 wherein said release surface means comprises a polymeric film affixed to said undergarment-facing surface of said central absorbent element.

5. The sanitary napkin of claim 4 wherein said film comprises a silicone-treated, thermoplastic web.

6. The sanitary napkin of claim 5 wherein said thermoplastic web comprises polyethylene.

7. The sanitary napkin of claim 2 wherein said adhesive means of each of said flaps comprises a pressure-sensitive adhesive.

8. The sanitary napkin of claim 7 wherein said pressure-sensitive adhesive comprises a hot melt composition.

9. The sanitary napkin of claim 6 wherein said thermoplastic web comprises a thickness of about 0.001 to about 0.125 inches (0.025-3.18 mm).

10. A sanitary napkin comprising:
(a) a central absorbent element having longitudinally extending sides, transverse ends, a body-facing side and an undergarment-facing surface, said undergarment-facing surface comprising a release surface disposed approximately midway between said transverse ends, said release surface being permanently formed on said undergarment-facing surface, and
(b) flaps extending laterally from each of said longitudinal sides of said absorbent element, each of said flaps comprising individual adhesive means disposed to contact said release surface when said flaps are folded onto said undergarment-facing surface of said absorbent element.

11. The sanitary napkin of claim 10 wherein said central absorbent element comprises adhesive means disposed on said undergarment-facing surface.

12. The sanitary napkin of claim 11 wherein said adhesive means of said central absorbent element comprises a pair of positional adhesive elements disposed proximate to said transverse ends of said sanitary napkin.

13. The sanitary napkin of claim 12 wherein said flaps are folded onto said undergarment facing surface of said central absorbent element so as to releasably attach said individual adhesive means of said flaps to said release surface of said undergarment facing surface of said central absorbent element.

14. A method of applying a sanitary napkin comprising:
(a) providing a sanitary napkin comprising a central absorbent element having longitudinally extending sides, transverse ends, a body-facing side and an undergarment-facing side, said undergarment-facing side comprising adhesive means and a release surface disposed approximately midway between said transverse ends, said sanitary napkin further comprising flaps extending laterally from each of said longitudinal sides of said central absorbent element, said flaps comprising individual adhesive means, said flaps being folded onto said undergarment-facing side of said central absorbent element so as to releasably attach said individual adhesive means of said flaps to said release surface;
(b) attaching said adhesive means of said central absorbent element to an undergarment.

15. The method of claim 14 further comprising releasing said individual adhesive means of said flaps from said release surface.

16. The method of claim 15 further comprising wrapping said flaps around a crotch area of said undergarment and attaching said individual adhesive means of said flaps to said undergarment.

17. A sanitary napkin comprising:
(a) a central absorbent element having longitudinally extending sides, transverse ends, a body-facing side and an undergarment-facing surface, said undergarment-facing surface comprising a pair of adhesive elements disposed near said transverse ends and a release surface disposed between said adhesive elements, said release surface being permanently attached to said undergarment-facing surface; said adhesive elements disposed to contact said release surface when said transverse ends are folded onto said undergarment-facing surface; and
(b) flaps extending laterally from each of said longitudinal sides of said central absorbent element, said flaps comprising individual adhesive means disposed to contact said release surface when said flaps are folded onto said undergarment-facing surface of said absorbent element.

* * * * *